(12) United States Patent
Chun et al.

(10) Patent No.: US 10,139,316 B1
(45) Date of Patent: Nov. 27, 2018

(54) BOTTOM SAMPLER

(71) Applicant: Korea Institute Of Geoscience And Mineral Resources, Daejeon (KR)

(72) Inventors: Jong-Hwa Chun, Daejeon (KR); Yu-Ri Kim, Daejeon (KR); Young-Sang Eo, Siheung-si (KR); Joo-Yong Lee, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 0 days.

(21) Appl. No.: 15/841,409

(22) Filed: Dec. 14, 2017

(30) Foreign Application Priority Data

Aug. 9, 2017 (KR) .......................... 10-2017-0100969

(51) Int. Cl.
*G01N 1/08* (2006.01)
(52) U.S. Cl.
CPC ..................................... *G01N 1/08* (2013.01)
(58) Field of Classification Search
CPC ................................. E21B 25/18; E21B 7/124
See application file for complete search history.

(56) References Cited

U.S. PATENT DOCUMENTS

| 2,638,321 | A | * | 5/1953 | Isbell | ..................... E21B 7/1245 |
| | | | | | 175/4 |
| 3,301,336 | A | * | 1/1967 | Mount | ................... E21B 7/1245 |
| | | | | | 175/135 |
| 3,370,566 | A | * | 2/1968 | Dorr | ........................ B63B 21/26 |
| | | | | | 114/295 |
| 3,716,107 | A | * | 2/1973 | Liautad | .................... E21B 25/18 |
| | | | | | 175/248 |
| 6,196,333 | B1 | * | 3/2001 | Aardal | .................... E21B 7/124 |
| | | | | | 175/5 |
| 6,390,206 | B1 | * | 5/2002 | Aardal | .................... E21B 25/18 |
| | | | | | 175/58 |

(Continued)

FOREIGN PATENT DOCUMENTS

| KR | 10-0838659 B1 | 6/2008 |
| KR | 10-2013-0022063 A | 3/2013 |

(Continued)

OTHER PUBLICATIONS

Korean Notice of Allowance for Korean Patent Application No. 10-2017-0100969 dated Aug. 30, 2017.

*Primary Examiner* — Paul West
*Assistant Examiner* — Mark A Shabman
(74) *Attorney, Agent, or Firm* — Harness, Dickey & Pierce, P.L.C.

(57) ABSTRACT

The present invention relates to a bottom sampler comprising, a cable connecting plate, an outer fixing plate disposed at a lower side of the cable connecting plate, a sample barrel guide extending downwards from the outer fixing plate, and a sample barrel configured to have a sediment permeation prevention plate mounted at an outer peripheral end, and provided with a valve at opposite ends, the valve connected to a guide rod pivotally coupled to a first end of a lever operating arm, wherein the valve is closed depending on the pivoting of the lever operating arm when a seabed sample is introduced into the sample barrel to seal an inner part thereof. Accordingly, seabed samples such as gas-filled sediments can be collected and analyzed without pressure leakage.

12 Claims, 7 Drawing Sheets

(56) References Cited

U.S. PATENT DOCUMENTS 7,681,662 B2 * 3/2010 Asakawa ................ E21B 7/124
    175/20
8,074,739 B2 * 12/2011 Sun .......................... G01N 1/08
    175/17

FOREIGN PATENT DOCUMENTS

| KR | 10-1361142 B1 | 2/2014 |
| KR | 10-1368908 B1 | 3/2014 |
| KR | 10-1577323 B1 | 12/2015 |

* cited by examiner

BOTTOM SAMPLER

CROSS-REFERENCE TO RELATED APPLICATION

This application claims priority to Korean Patent Application No. 10-2017-0100969 filed on Aug. 9, 2017, and all the benefits accruing therefrom under 35 U.S.C. § 119, the contents of which is incorporated by reference in its entirety.

BACKGROUND OF THE INVENTION

1. Field of the Invention

The present disclosure relates to a bottom sampler capable of sampling seabed samples such as gas-filled sediments near the seabed.

2. Description of the Related Art

Seafloor (ocean and lake) sediments contain a lot of organic matter, and gas (methane, hydrogen sulfide, carbon dioxide) is generated by decomposition and decay of organic matter. The pores of seafloor sediments containing much organic matter are filled with gas.

In particular, gas hydrates are solids that are stable under the conditions of low temperature and high pressure, packed with gas molecules in a basket-shaped structure formed by water molecules. It has been confirmed that the gas hydrate containing methane molecules as a main component is present in the permafrost and the sediment layers of the seafloor. As a method for researching gas hydrate, there is a method known as the seismic exploration method in which a seismic wave like that of a seismic source is generated to survey the values of reflection from a sediment layer. Using this method, the distribution situation of gas hydrate present in nature is being surveyed.

Since excavating a sediment layer as well as using various sensors to examine the physical properties necessary for evaluation of the resource amount or productivity of gas is being done, surveying the physical properties of a sediment sample of a gas hydrate by collecting sediment as desired is also done frequently.

Various devices have been introduced to collect these sediment samples. Conventionally, piston corers, gravity corers, and grabs were used. However there is the problem of gas leaking, ambient air being injected, or the sediment being expanded by gas, due to lowered pressure and raised temperature in the process of collecting sediments from the seabed to sand it up to the ship and treating the sediments on the ship.

In particular, since a gas hydrate exists in the form of ice with gas and water combined in a high pressure and low temperature environment, in the process of collecting the gas hydrate developed on the seabed to the ship by using a conventional sediment sampling apparatus, dissociation (physical separation from gas) occurs rapidly. Thereby, there is a risk in the safety of the collecting work, and the gas hydrate sample is contaminated.

Meanwhile, in regions where active submarine volcanic eruption occur, a large amount of volcanic gases (carbon dioxide, nitrogen, sulfur dioxide) are contained in the seabed sediments around the crater. Depending on the amount and type of volcanic gas, data on volcanic activity can be obtained, but when existing sediment sampling apparatuses, gas may leak or deformation of sediments may occur.

A pressure corer that maintains pressure to prevent gas emission can be applied to large-scale drilling rigs in drilling ships that are expensive and require many workers, but the pressure corer cannot collect sediments on its own, and there is the problem that it must use large-scale drilling rigs.

In addition, drilling rigs of drilling ships are not designed to collect sediments near the seabed, and it is impossible to utilize drilling ships in ocean or lakes where the water depth is shallow.

Therefore, there is an urgent need for the development of a sampler capable of collecting samples for a simple lifting device as well as a drilling ship, while preventing contamination of the sample by preventing gas emission with a simpler structure.

As a prior art related thereto, there is a safety device for sample collection device disclosed in Korean Granted Patent Publication No. 1361142 (published on Feb. 13, 2014).

SUMMARY OF THE INVENTION

Therefore, the present disclosure is directed to maintain the seabed pressure and prevent gas from leaking or sediments from expanding when collecting gas-filled sediments that are near the seabed onboard by using a tensioning device such as a cable in a ship winch.

The problems to be solved by the present disclosure are not limited to the above-mentioned problem(s), and other problem(s) not mentioned can be clearly understood by those skilled in the art from the following description.

According to an exemplary embodiment of the present disclosure, a bottom sampler may include, a cable connecting plate provided with a plurality of connecting parts that connect to a cable at an upper part and a retaining pin at a lower part; an outer fixing plate disposed at a lower side of the cable connecting plate, provided with a landing trigger that is fastened to the retaining pin by pivoting about a first rotational axis provided on one side; a sample barrel guide extending downwards from the outer fixing plate, configured to have a second rotational axis disposed at a center thereof, provided with, a pair of lever operating arms that pivot about the second rotational axis, a weight supporting plate mounted at a lower end portion of the second rotational axis to seat a weight, and a fastening part at a lower end of the weight supporting plate; and a sample barrel, which is fastened and connected to the fastening part, and configured to have a sediment permeation prevention plate mounted at an outer peripheral end, and provided with a valve at opposite ends, the valve connected to a guide rod pivotally coupled to a first end of a lever operating arm, wherein the valve is closed depending on the pivoting of the lever operating arm when a seabed sample is introduced into the sample barrel to seal an inner part thereof.

Further, the cable may be extended from the connecting part to be connected to a second end of the lever operating arm, and depending on the elevation of the cable connecting plate the second end of the lever operating arm may be pivoted to apply a load to the first end of the lever operating arm.

Further, the outer fixing plate may be provided with a safety pin which passes through and fixes one end of the landing trigger while the landing trigger is fastened to the retaining pin.

Further, the lever operating arm may be pivoted about the second rotational axis, and a distance from the second rotational axis to the second end may be extended to be longer than a distance from the second rotational axis to the first end.

Further, the weight supporting plate may have a plurality of support bars along the circumference thereof, and a plurality of weights may pass through and be inserted into the support bars, and then the weights may be fixed by fastening means provided at the ends of the support bars.

Further, the fastening part may connect the sample barrel guide and the sample barrel, and may be provided with a plurality of fastening protrusions at one end of the sample barrel guide, and a plurality of fastening recesses to be fastened in correspondence with the fastening protrusions may be formed and connected at one end of the sample barrel.

Further, the valve may be a ball valve that is opened or closed by the operation of an external lever.

Further, the valve may be provided with an opening and closing lever on an outer part and a connection guide may be pivotally coupled to an end of the opening and closing lever, and one end of the connection guide may be fastened to the guide rod to close the valve depending on a vertical movement of the guide rod.

Further, the sediment permeation prevention plate may have a plurality of holes formed along a circumference thereof to allow seawater to pass through, and may prevent the sample barrel from penetrating into the seabed to a depth more than or equal to its length when the sample barrel is seated on the seabed.

Further, the sample barrel may have a pressure outlet formed at one end thereof, and pressure may be adjusted by discharging gas therein.

According to the present disclosure, the sediment sampling apparatus which maintains seabed pressure may use a lifting device such as a winch to collect samples of gas-filled sediments or gas hydrates near a seabed (lakebed).

The pressure corer operated in a conventional drilling ship may be replaced to maintain the pressure of a seabed having a depth of a several thousand feet and gas-filled sediments or gas hydrates can be sampled at a low cost and high efficiency.

In addition, it is possible to separate and transport or store sample barrels that maintain seabed pressure, and via computerized tomography of the sample barrels the sediment structure of the sampling site can be identified.

Meanwhile, by sampling a gas sample directly through the pressure outlet of the sample barrel, contamination of the sample due to various operations can be prevented.

In addition, since the structure is simplified and reduced in size, it can be connected to a winch of a drilling ship to be operated and thus, the scale of the apparatus is not large, and it is advantageous to be utilized not only at sea, but also in a shallow water depth environment such as a lake and a river.

DETAILED DESCRIPTION OF THE INVENTION

Hereinafter, the present invention will be described more fully with reference to the accompanying drawings, in which exemplary embodiments of the invention are shown.

The present disclosure and methods of accomplishing the same may be understood more readily by reference to the following detailed description of embodiments and the accompanying drawings. However, the present disclosure may be embodied in many different forms, and should not be construed as being limited to the embodiments set forth herein. Rather, these embodiments are provided so that this disclosure will be thorough and complete and will fully convey the concept of the invention to those skilled in the art, and the present disclosure will only be defined by the appended claims.

In addition, when it is determined that there is a known technology and the like in regards to describing the present disclosure which may blur the point of the present disclosure, detailed description thereof will be omitted.

Figure 1:
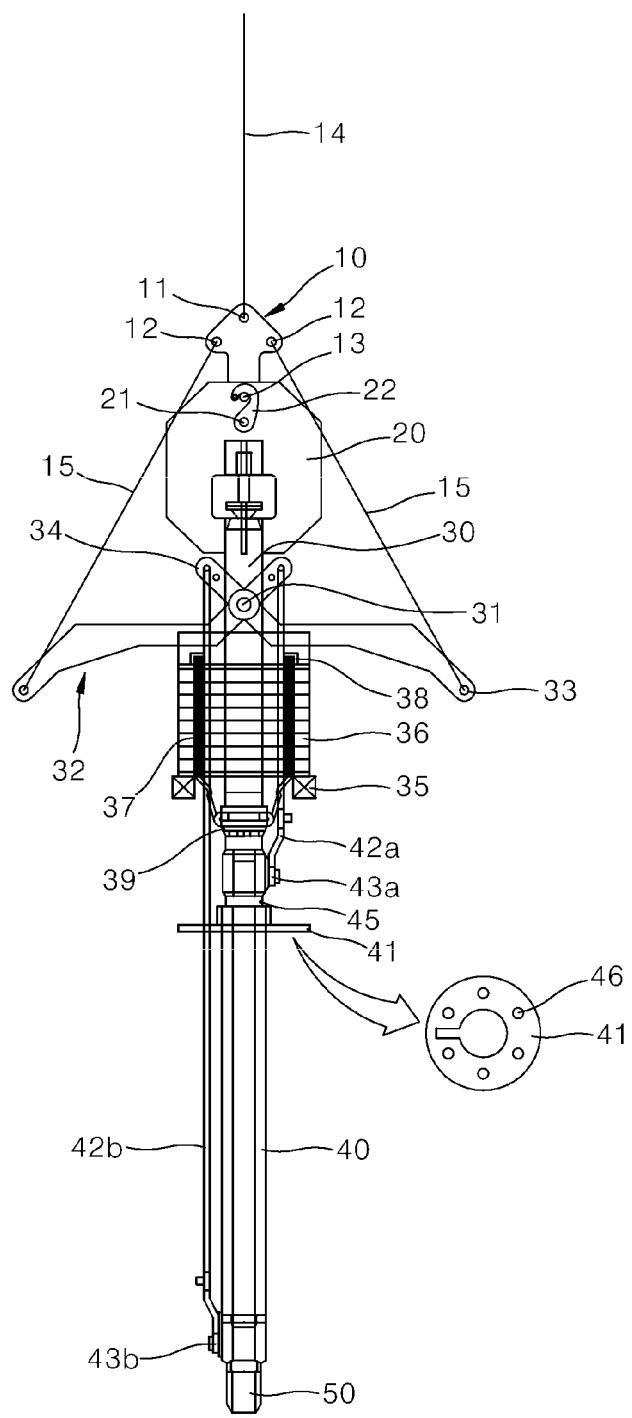
FIG. 1 is a side view of a bottom sampler according to an exemplary embodiment of the present disclosure.

FIG. 1 is a side view of a bottom sampler according to an exemplary embodiment of the present disclosure.

Referring to FIG. 1, a bottom sampler according to the present disclosure includes a cable connecting plate, an outer fixing plate, a sample barrel guide, and a sample barrel.

The cable connecting plate 10 is provided with a plurality of connecting parts 11, 12 that connect to a cable at an upper part and a retaining pin 13 at a lower part.

The cable connecting plate 10 is provided with a plurality of connecting parts 11, 12 and some connecting parts 11 are directly connected to a cable 14 of a lifting device provided in a ship such as a winch to support a bottom sampler in a vertical direction.

A cable 15 is extended from the connecting part 12 to be connected to a second end 33 of the lever operating arm, and depending on the elevation of the cable connecting plate 10 the second end 33 of the lever operating arm may be pivoted to apply a load to a first end 34 of the lever operating arm.

The cables 14, 15 are classified as a winch cable 14 connected to the winch of a ship and a cable 15 directly connected to the lever operating arm 32.

A retaining pin 13 is provided at a lower part of the cable connecting plate 10.

The outer fixing plate 20 is disposed at a lower side of the cable connecting plate 10, and provides an inner space where a landing trigger 22 and a sample barrel guide 30 may be mounted.

The outer fixing plate 20 is provided with a first rotational axis 21 at one side.

The landing trigger 22 pivots about the first rotational axis 21 and may be fastened to the retaining pin 13, and at this time, the cable connecting plate 10 and outer fixing plate 20 may be connected.

Figure 2:
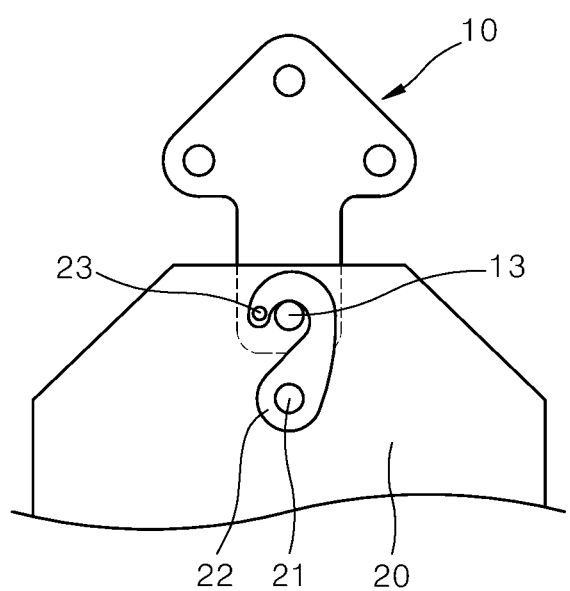
FIG. 2 is an enlarged side view of a connection portion of a cable connecting plate and outer fixing plate of the bottom sampler of FIG. 1.

FIG. 2 is an enlarged side view of a connection portion of a cable connecting plate and outer fixing plate of the bottom sampler of FIG. 1.

Referring to FIG. 2, at one side of the outer fixing plate 20, a safety pin 23 may be provided.

The safety pin 23 passes through one end of the landing trigger 22 while the landing trigger 22 is fastened to the retaining pin 13 and fixes the landing trigger 22 to prevent it from pivoting.

Because the cable connecting plate 10 and the outer fixing plate 20 is maintained in a connected state when the safety pin 23 is in a fastened state, the landing trigger 22 can safely perform the transportation and storage of the bottom sampler in a fastened state.

When the safety pin 23 is in a released state and the bottom sampler reaches the seabed, the tension of the cable 14 decreases and the cable connecting plate 10 is lowered and the friction between the landing trigger 22 and the retaining pin 13 decreases, thereby the landing trigger 22 may be released from the retaining pin 13.

The sample barrel guide 30 is extended downwards from the outer fixing plate 20, configured to have a second rotational axis 31 disposed at a center thereof, and is provided with a pair of lever operating arms 32 that pivot about the second rotational axis 31.

Each of the pair of lever operating arms 32 is symmetrically provided with respect to the second rotational axis 31, and depending on the vertical movement of the cable 15 connected to a second end 33 of the lever operating arm, a first end 34 of the lever operating arm may be pivoted.

The lever operating arm 32 is pivoted about the second rotational axis 31, and a distance from the second rotational axis 31 to a second end is extended to be longer than a distance from the second rotational axis 31 to a first end.

The distance from the second rotational axis 31 to a second end is extended to be longer than the distance from the second rotational axis 31 to a first end, enabling the load delivered to the first end 34 of the lever operating arm to be increased very efficiently so the first end 34 of the lever operating arm is strongly pivoted when the cable 15 is elevated and the second end 33 of the lever operating arm is lifted vertically.

The cable 15 pulls the second end 33 of the lever operating arm to pivot the second end of the lever operating arm and the lever operating arm 32 is accommodated in the outer fixing plate 20 in the lifting process of the bottom sampler.

In the case where the second end 33 of the lever operating arm is accommodated in the outer fixing plate 20, in the process of lifting the bottom sampler, the lever operating arm 32 is protected, and the working space for the separating process of the sample barrel 40 is decreased, and the efficiency of the seabed sampling work is increased.

Meanwhile, the sample barrel guide 30 is configured to have a weight supporting plate 35 mounted at a lower end portion of the second rotational axis 31 to seat a weight 36, and a fastening part 39 provided at a lower end of the supporting plate.

The weight 36 increases the weight of the bottom sampler so that the sample barrel 40 passes through the seawater and touches the seabed, and then penetrates the surface layer of the seabed.

Since the surface layer of the seabed is very loose, if the weight of the weight 36 is applied, the sample barrel 40 can penetrate the surface layer of the seabed to introduce the sediment into the sample barrel 40.

The weight supporting plate 35 has a plurality of support bars 37 along the circumference thereof, and the plurality of support bars 37 may pass through a plurality of weights 36 and be inserted into the plurality of weights 36, and the weights 36 are fixed by fastening means 38 provided at both ends of the support bars 37.

The weight supporting plate 35 may be formed to surround the circumference of the sample barrel guide 30 and may be formed as a disc or a rectangular plate depending on the shape of the weights 36.

A plurality of support bars 37 may be provided on a surface of the weight support plate 35.

Through-holes (not specifically designated) are formed through the weights 36, and the support bars 37 are inserted the through-holes of the weights 36 such that the weights 37 are seated on the weight supporting plate 35.

After the weights 36 are fixed by the support bar 37 penetrating through the weights 36, the weights 36 may be firmly fixed by the fastening means 38.

In the case where the support bar 37 is provided as a bolt, the fastening means 38 may be provided as a nut, and so it is very preferable in fixing the weights 36. However, the fastening means for allowing the easy attachment and detachment of the weights 36 is not limited thereto.

The fastening means 38 are provided, making it easier to add and subtract weight 36, thereby it is possible to collect samples by adding and subtracting weight 36 depending on the hardness of the surface layer of the seabed when collecting seabed samples.

The fastening part 39 is provided at a lower portion of the weight supporting plate 35.

The fastening part 39 connects the sample barrel guide 30 and the sample barrel 40 together.

The fastening part 39 is provided, and it is possible to collect gas-filled sediments on a ship by separating the sample barrel 40 and the sample barrel guide 30 after collecting the seabed samples, and it is possible to transport the sample barrel as it is, allowing analysis or refrigeration storage, thereby enabling the prevention of sample contamination.

In the conventional pressure corer, there is no means for separating the sample tube, so that when the pressure is released and the inside of the sample tube is analyzed, there is a risk of gas leakage and the sample may be contaminated. However, the accuracy of sample testing is greatly increased when the sample barrel 40 is separated in a sealed state.

In addition, the conventional pressure corers require a considerable amount of time and preparation for reuse after sampling. However, the bottom sampler can be continuously sampled by replacing the sample barrel 40, and gas-filled sediments of a different region may be collected, making it possible to conduct a full-scale exploration of the seabed.

Figure 3:
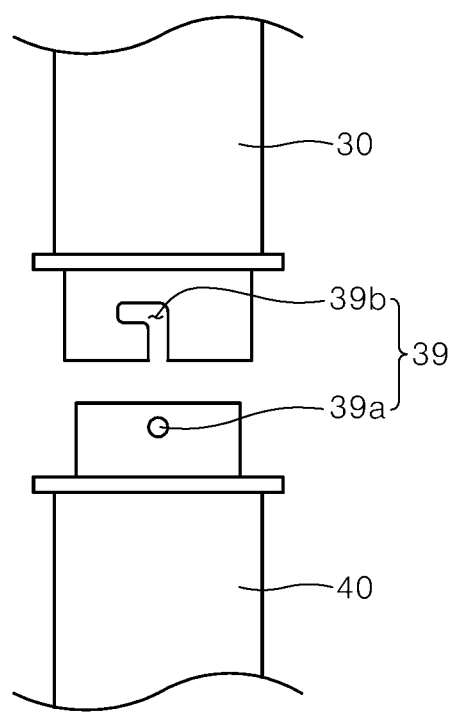
FIG. 3 is a side view of a fastening part of the bottom sampler of FIG. 1.

FIG. 3 is a side view of a fastening part of the bottom sampler of FIG. 1.

Referring to FIG. 3, the fastening part 39 of a detailed exemplary embodiment of the present disclosure is provided with a plurality of fastening protrusions 39a at one end of the sample barrel 40, and a plurality of fastening recesses 39b configured to be fastened in correspondence with the fastening protrusions 39a may be formed and connected at one end of the sample barrel 30, which faces the one end of the sample barrel guide 40.

In the case where the fastening part 39 is a structure wherein the fastening protrusions are fastened in correspondence with the fastening recesses, the fastening process is easy and the time it takes for releasing to separate the fastening protrusion can be significantly shortened. However, the present disclosure is not limited thereto as long as the fastening part 39 is a means for fastening to fix the sample barrel 40 and the sample barrel guide 30 together or for releasing to separate the same.

The sample barrel 40 is fastened and connected to the fastening part 39, and a sediment permeation prevention plate 41 is mounted at an outer peripheral end thereof.

The sediment permeation prevention plate 41 has a plurality of holes 45 formed along a circumference thereof to allow seawater to pass through, and can prevent the sample barrel 40 from penetrating into the seabed to a depth more than or equal to its length when the sample barrel 40 is seated on the seabed.

Therefore when the bottom sampler is lowered in seawater to land on the seabed, a seabed sample can be collected from the surface layer of the seabed to a depth corresponding to the length of the sample barrel 40.

The sample barrel 40 is provided with valves 43*a* and 43*b* at opposite ends, and the valves 43*a* and 43*b* are connected to guide rods 42*a* and 42*b* pivotally coupled to the first ends 34 of the lever operating arms.

The valves 43*a* and 43*b* may be ball valves that are opened or closed by the operation of an external lever.

In the case where ball valves are selected to be the valves 43*a* and 43*b*, the sample barrel 40 can be sealed after the sample is introduced into the sample barrel 40 just by the operation of an external lever.

In the case where the sample barrel 40 is sealed by the ball valves, it is advantageous in that pressure can be constantly maintained while the bottom sampler is lifted to the seawater surface.

Figure 4:
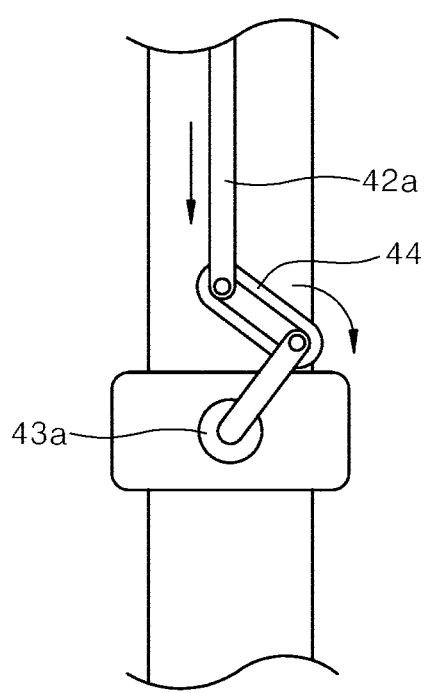
FIG. 4 is a front view showing a valve of a sample barrel of the bottom sampler of FIG. 1.

FIG. 4 is a front view showing a valve of a sample barrel of the bottom sampler of FIG. 1.

Referring to FIG. 4, in a detailed exemplary embodiment of the present disclosure, a valve is provided with an opening and closing lever on an outer part and a connection guide 44 is pivotally coupled to an end of the opening and closing lever, and one end of the connection guide 44 is fastened to the guide rod 42*a* and the valve 43*a* may be closed depending on a vertical movement of the guide rod 42*a*.

When the first end 34 of the lever operation arm is lowered, the connected guide rods 42*a* and 42*b* are lowered vertically, and as the lever fastened to the guide rods 42*a* and 42*b* rotate, the balls inside the ball valves are rotated and can seal the sample barrel 40.

In the case where the sample barrel 40 is sealed, even when gas of the gas-filled sediment expands as the sample barrel 40 is elevated to the seawater surface, the gas is not discharged and the sample barrel 40 can be lifted stably.

The sample barrel 40 has a pressure outlet 45 formed at one end thereof, and pressure can be adjusted by discharging the gas therein.

The pressure outlet 45 can separate and discharge vaporized gas from the gas-filled sediment to collect the gas. The inner pressure of the sample barrel 40 is lowered to obtain a sample filled therein.

The sample barrel 40 is configured to have a barrel head 50 mounted at an end facing the seabed 60.

The barrel head 50 may be provided as a steel material because it is a portion that must collide with the surface layer of the seabed 60 when falling and penetrate into the surface layer. Also, the diameter of the barrel head 50 may be provided to gradually decrease toward the front end to make the penetration into the seabed more advantageous.

The sample barrel 40 may be an aluminum alloy that can be analyzed by X-ray or CT.

Since the sample barrel 40 can be separated and transported from the sample barrel guide 30, when it is made of an aluminum alloy, it is possible to analyze gas-filled sediments filled therein, directly by X-ray or CT on the ship.

Hereinafter, an operation method of the bottom sampler of the present disclosure will be described as follows.

Figure 6A:
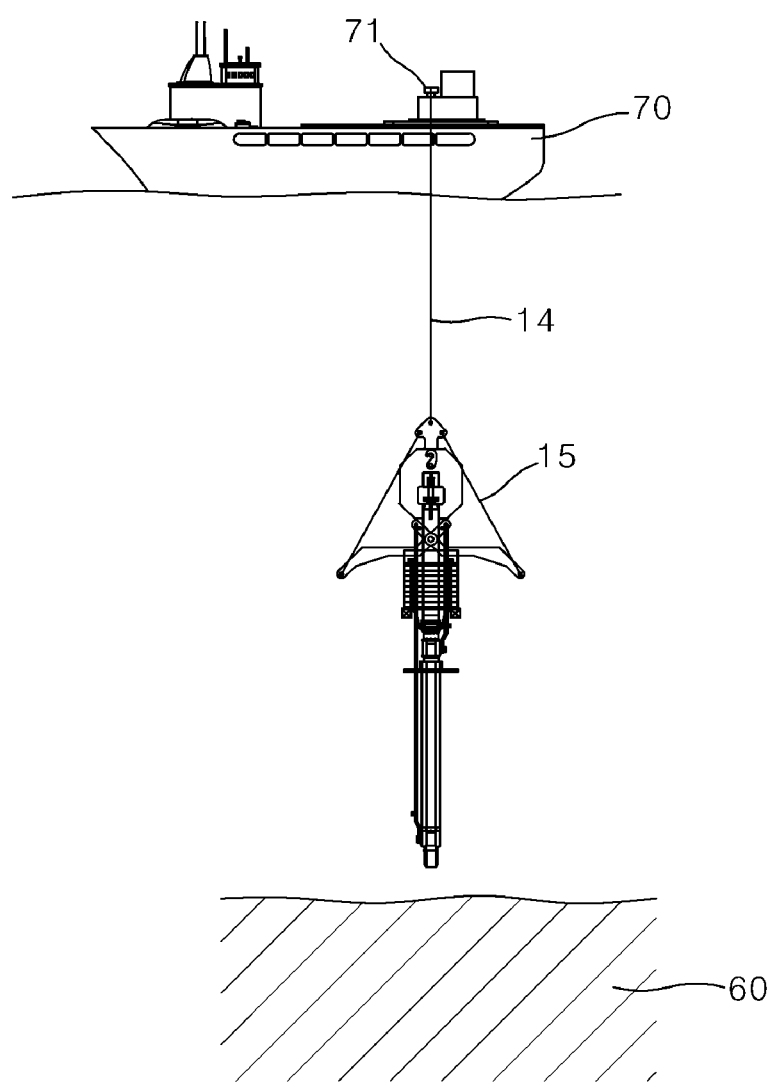
FIG. 6A is a view showing the state of a sample barrel according an exemplary embodiment of the present disclosure being used.
Figure 6B:
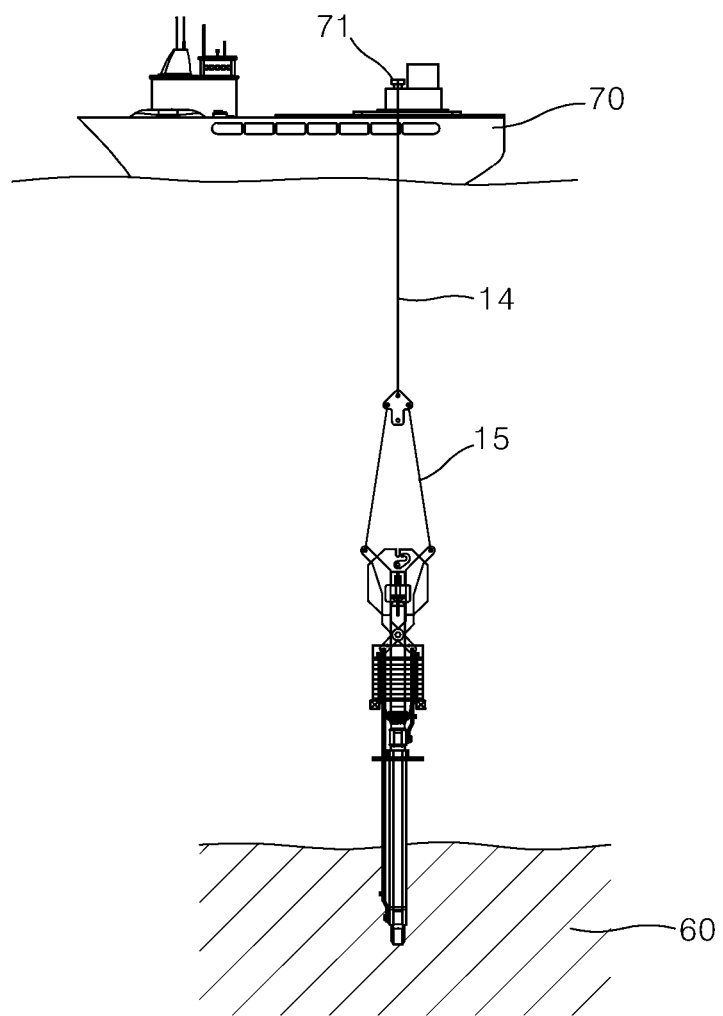
FIG. 6B is a view showing the state of a sample barrel according an exemplary embodiment of the present disclosure being used.

FIG. 6A is a view showing the state of a sample barrel according an exemplary embodiment of the present disclosure being used, and FIG. 6B is a view showing the state of a sample barrel according an exemplary embodiment of the present disclosure being used.

Referring to FIGS. 6A and 6B, the bottom sampler is connected to a winch 71 of a ship 70 for collecting seabed samples such as gas-filled sediments or gas hydrates and the like.

After the safety pin 23 inserted in the outer fixing plate 20 is removed, the winch of the ship is used to lower the bottom sampler under the seawater surface.

At this time, the bottom sampler is lowered due to its weight and penetrates and is inserted in the surface layer of the seabed using the speed it is lowered by.

While the sample barrel 40 penetrates the seabed 60, the valve of the sample barrel 40 is maintained at an open state to allow the seabed sample to be introduced right into the sample barrel 40.

When the sample barrel 40 penetrates the seabed up to where the sediment permeation prevention plate 41 is, the sample barrel 40 can no longer penetrate the seabed, and when the cable connecting plate 10 is lowered more, the landing trigger 22 is disengaged from the retaining pin 13.

Figure 5:
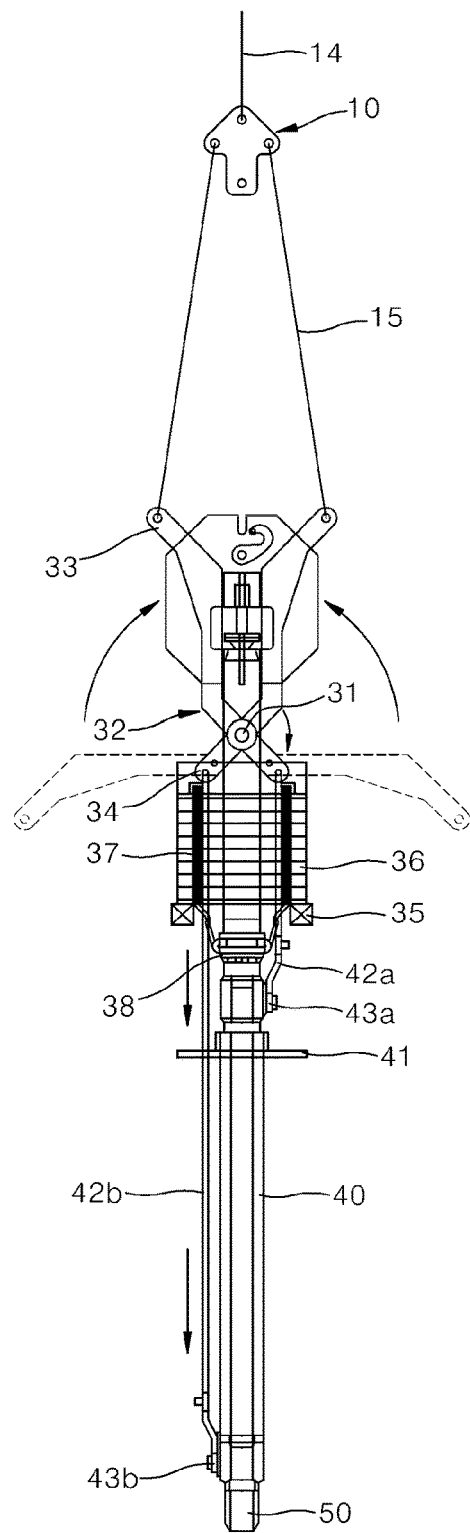
FIG. 5 is a side view showing a sealed state of a sample barrel according to an exemplary embodiment of the present disclosure.

FIG. 5 is a side view showing a sealed state of a sample barrel according to an exemplary embodiment of the present disclosure.

Referring to FIG. 5, when it is determined that the bottom sampler penetrated the surface layer of the seabed, the winch 71 of the ship 70 is winded to pull the cable 14.

The cable connecting plate 10 is elevated and the cable 15 of the connecting part of the cable connecting plate 10 elevates the second end 33 of the lever operating arm.

When the second end 33 of the lever operating arm is elevated, the first end 34 of the lever operating arm is lowered with respect to the second rotational axis 31 and the guide bars 42*a* and 42*b* are lowered.

The distance from the center of the second rotational axis 31 to the second end 33 of the lever operating arm is longer than the distance from the center of the second rotational axis 31 to the first end 34 of the lever operating arm, and therefore the first end 34 of the lever operating arm can be lowered only with the pulling force of the cable.

When the guide bars are lowered vertically, the connection guide 44 fastened to the guide bars rotate to close all the valves 43*a* and 43*b*.

Accordingly, when the cable 14 is lifted, due to the pivoting of the lever operating arm 32, the valves 43*a* and 43*b* of opposite ends of the sample barrel 40 are closed all at once and the sample barrel 40 can be sealed.

After lifting the sample barrel 40, the pressure outlet 45 is opened and the expanded gas can be recovered and collected, and after the gas is completely discharged, the sample inside the sample barrel 40 can be recovered and analyzed.

Because the sample barrel 40 can be separated from the sample barrel guide 30, the sample barrel 40 can be separated and a new sample barrel 40 can be mounted to continuously collect seabed samples.

The sample barrel 40 may be formed of aluminum alloy material, through which X-ray or CT can be transmitted to enable the immediate determination of the structure and physical properties of gas-filled sediment as a sample on a ship.

In addition, the sample barrel 40 can be separated and transported, allowing easy refrigeration storage for detailed analysis of the sample.

Although the bottom sampler according to the detailed exemplary embodiment of the present disclosure has been described above, it is apparent that various modifications can be made without departing from the scope of the present disclosure.

Therefore, the scope of the present disclosure should not be limited to the embodiments described, but should be determined by equivalents to the scope of the appended claims, as well as the appended claims.

In other words, it is to be understood that the above-described embodiments are illustrative in all aspects and should not be construed as limiting, and the scope of the present disclosure is indicated by the appended claims rather than the detailed description, And all equivalents and variations that come within the meaning and range of equivalency of the claims are to be embraced within their scope.

What is claimed is:

1. A bottom sampler comprising,
a cable connecting plate provided with a plurality of connecting parts that connect to a cable at an upper part and a retaining pin at a lower part;
an outer fixing plate at a lower side of the cable connecting plate, the outer fixing plate provided with a landing trigger, the landing trigger configured to be fastened to the retaining pin by pivoting about a first rotational axis provided on one side of the outer fixing plate;
a sample barrel guide extending downwards from the outer fixing plate, the sample barrel guide configured to have a second rotational axis at a center thereof, the sample barrel guide provided with a pair of lever operating arms that are configured to pivot about the second rotational axis, a weight supporting plate mounted at a lower end portion of the second rotational axis to seat a weight, and a fastening part at a lower end of the weight supporting plate; and
a sample barrel, which is fastened and connected to the fastening part, configured to have a sediment permeation prevention plate mounted at an outer peripheral end, and provided with valves at opposite ends, each of the valves connected to a guide rod pivotally coupled to a first end of a lever operating arm,
wherein the valves are configured to be closed depending on pivoting of the lever operating arm when a seabed sample is introduced into the sample barrel to seal an inner part thereof.

2. The bottom sampler of claim 1, wherein the cable is connected to each of the connecting parts and a second end of the lever operating arm, and the second end of the lever operating arm is configured to be rotated to apply a load to the first end of the lever operating arm depending on elevation of the cable connecting plate.

3. The bottom sampler of claim 1, wherein the outer fixing plate is provided with a safety pin which passes through and fixes one end of the landing trigger while the landing trigger is fastened to the retaining pin.

4. The bottom sampler of claim 1, wherein the lever operating arm is pivotable about the second rotational axis, and a distance from the second rotational axis to a second end of the lever operating arm is longer than a distance from the second rotational axis to the first end.

5. The bottom sampler of claim 1, wherein the weight supporting plate has a plurality of support bars along a circumference thereof, and the plurality of support bars pass through a plurality of weights pass through and are inserted into the plurality of weights, and the weights are fixed by a fastener provided at both ends of the support bars.

6. The bottom sampler of claim 1, wherein the fastening part connects the sample barrel guide and the sample barrel, and is provided with a plurality of fastening protrusions at one end of the sample barrel, and a plurality of fastening recesses at one end of the sample barrel guide and configured to be fastened to the fastening protrusions, the one end of the sample barrel facing the one end of the sample barrel guide.

7. The bottom sampler of claim 1, wherein the valves are ball valves that are configured to be opened or closed by the operation of an external lever.

8. The bottom sampler of claim 1, wherein each of the valves is provided with an opening and closing lever on an outer part thereof and a connection guide is pivotally coupled to an end of the opening and closing lever, and one end of the connection guide is fastened to the guide rod to close each of the valves depending on a vertical movement of the guide rod.

9. The bottom sampler of claim 1, wherein the sediment permeation prevention plate has a plurality of holes formed along a circumference thereof to allow seawater to pass through, and prevent the sample barrel from penetrating into a seabed to a depth more than or equal to its length when the sample barrel is seated on the seabed.

10. The bottom sampler of claim 1, wherein the sample barrel has a pressure outlet at one end thereof, and is configured to adjust pressure by discharging gas therein through the pressure outlet.

11. The bottom sampler of claim 1, wherein the sample barrel is configured to have a barrel head at an end facing a seabed.

12. The bottom sampler of claim 1, wherein the sample barrel is formed of an aluminum alloy that can be analyzed by X-ray or CT.

* * * * *